(12) United States Patent
Young et al.

(10) Patent No.: US 11,957,719 B2
(45) Date of Patent: *Apr. 16, 2024

(54) PHENOTYPE PROFILE OF HUMAN RETINAL PROGENITOR CELLS

(71) Applicant: THE SCHEPENS EYE RESEARCH INSTITUTE, Boston, MA (US)

(72) Inventors: Michael J. Young, Gloucester, MA (US); Petr Y. Baranov, Somerville, MA (US)

(73) Assignee: The Schepens Eye Research Institute, Boston, MA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/823,841

(22) Filed: Mar. 19, 2020

(65) Prior Publication Data

US 2020/0345785 A1 Nov. 5, 2020

Related U.S. Application Data

(63) Continuation of application No. 14/379,239, filed as application No. PCT/US2013/026286 on Feb. 15, 2013, now Pat. No. 10,758,572.

(60) Provisional application No. 61/600,288, filed on Feb. 17, 2012.

(51) Int. Cl.
| | | |
|---|---|---|
| *A61K 35/30* | (2015.01) | |
| *C12N 5/079* | (2010.01) | |
| *C12N 5/0793* | (2010.01) | |
| *G01N 33/569* | (2006.01) | |

(52) U.S. Cl.
CPC .............. *A61K 35/30* (2013.01); *C12N 5/062* (2013.01); *C12N 5/0621* (2013.01); *G01N 33/56966* (2013.01); *G01N 2333/46* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,359,045 A | 10/1994 | Soubrier et al. |
| 5,359,046 A | 10/1994 | Capon et al. |
| 5,654,183 A | 8/1997 | Anderson et al. |
| 5,672,499 A | 9/1997 | Anderson et al. |
| 5,693,482 A | 12/1997 | Anderson et al. |
| 5,750,376 A | 5/1998 | Weiss et al. |
| 5,753,506 A | 5/1998 | Johe |
| 5,776,747 A | 7/1998 | Schinstine et al. |
| 5,795,790 A | 8/1998 | Schinstine et al. |
| 5,824,489 A | 10/1998 | Anderson et al. |
| 5,833,979 A | 11/1998 | Schinstine et al. |
| 5,840,576 A | 11/1998 | Schinstine et al. |
| 5,843,431 A | 12/1998 | Schinstine et al. |
| 5,843,432 A | 12/1998 | Klatzmann et al. |
| 5,849,553 A | 12/1998 | Anderson et al. |
| 5,851,832 A | 12/1998 | Weiss et al. |
| 5,853,717 A | 12/1998 | Schinstine et al. |
| 5,858,747 A | 1/1999 | Schinstine et al. |
| 5,861,283 A | 1/1999 | Levitt et al. |
| 5,928,947 A | 7/1999 | Anderson et al. |
| 5,935,849 A | 8/1999 | Schinstine et al. |
| 5,958,767 A | 9/1999 | Snyder et al. |
| 5,968,829 A | 10/1999 | Carpenter |
| 5,980,885 A | 11/1999 | Weiss et al. |
| 5,981,165 A | 11/1999 | Weiss et al. |
| 6,001,654 A | 12/1999 | Anderson et al. |
| 6,033,906 A | 3/2000 | Anderson |
| 6,071,889 A | 6/2000 | Weiss et al. |
| 6,093,531 A | 7/2000 | Bjornson et al. |
| 6,103,530 A | 8/2000 | Carpenter |
| 6,117,675 A | 9/2000 | van der Kooy et al. |
| 6,165,783 A | 12/2000 | Weiss et al. |
| 6,171,610 B1 | 1/2001 | Vacanti et al. |
| 6,184,035 B1 | 2/2001 | Csete et al. |
| 6,468,794 B1 | 10/2002 | Uchida et al. |
| 6,638,369 B1 | 10/2003 | Tucker et al. |
| 6,908,763 B1 | 6/2005 | Akashi et al. |
| 7,015,037 B1 | 3/2006 | Furcht et al. |
| 7,514,259 B2 | 4/2009 | Young et al. |
| 7,749,754 B2 | 7/2010 | Sherwood et al. |
| 7,781,179 B2 | 8/2010 | Weissman et al. |
| 8,563,304 B2 | 10/2013 | Young et al. |
| 2006/0223177 A1 | 10/2006 | Harris et al. |
| 2009/0170101 A1 | 7/2009 | Lewis et al. |
| 2009/0238800 A1 | 9/2009 | Lashkari et al. |

(Continued)

FOREIGN PATENT DOCUMENTS

| | | |
|---|---|---|
| WO | WO-94/09119 | 4/1994 |
| WO | WO-94/10292 | 5/1994 |

(Continued)

OTHER PUBLICATIONS

Schmitt et al., Investigative Ophthalmology & Visual Science, Dec. 2009, vol. 50, No. 12, pp. 5901-5908 (Year: 2009).*
Notice of Allowance dated May 28, 2020, from U.S. Appl. No. 14/379,239.
Aftab et al., "Growth kinetics and transplantation of human retinal progenitor cells," Experimental Eye Research, vol. 89, 2009, pp. 301-310.
Ahmad et al. (2000) "Progenitor Cell and Retinal Development: Before and After," Paper Presentation, JOVS, 41(4): Abstracts of Paper Presenations.

(Continued)

*Primary Examiner* — Evelyn Y Pyla
(74) *Attorney, Agent, or Firm* — Foley & Lardner LLP

(57) ABSTRACT

The present invention relates to substantially homogenous populations of human retinal progenitor cells having the following positive surface markers: SSEA4, CD73, PTK7 and PSA-NCAM. The invention also relates to method for preparing such substantially homogeneous cell populations from human tissue using cell sorting techniques.

12 Claims, 6 Drawing Sheets

(56) References Cited

U.S. PATENT DOCUMENTS

| | | | |
|---|---|---|---|
| 2009/0306772 | A1 | 12/2009 | Tao et al. |
| 2010/0318193 | A1 | 12/2010 | Desai et al. |
| 2011/0004304 | A1 | 1/2011 | Tao et al. |
| 2011/0043404 | A1 | 2/2011 | Weng et al. |
| 2011/0064701 | A1 | 3/2011 | Young et al. |
| 2011/0269173 | A1 | 11/2011 | Zhu et al. |
| 2012/0321593 | A1* | 12/2012 | Young .................. C12N 5/0623 424/93.7 |
| 2013/0189341 | A1 | 7/2013 | Regatieri et al. |
| 2014/0186309 | A1 | 7/2014 | Klassen et al. |
| 2015/0017133 | A1 | 1/2015 | Young et al. |

FOREIGN PATENT DOCUMENTS

| | | |
|---|---|---|
| WO | WO-94/16718 | 8/1994 |
| WO | WO-95/13364 A1 | 5/1995 |
| WO | WO-95/13365 A1 | 5/1995 |
| WO | WO-96/09543 A1 | 3/1996 |
| WO | WO-96/15226 A1 | 5/1996 |
| WO | WO-97/35605 | 10/1997 |
| WO | WO-99/21966 A1 | 5/1999 |
| WO | WO-99/55838 A1 | 11/1999 |
| WO | WO-00/47718 | 8/2000 |
| WO | WO-01/58460 A1 | 8/2001 |
| WO | WO-2011/028524 A1 | 3/2011 |
| WO | WO-2012/158910 A2 | 11/2012 |
| WO | WO-2012/177968 | 12/2012 |

OTHER PUBLICATIONS

Ahmad et al., "Identification of Neural Progenitors in the Adult Mammalian Eye," Biochemical and Biophysical Research Communications, vol. 270, No. 2, pp. 517-521.
Ahmad et al., 1999, Brain Research, 831: 1-10.
Baranov et al. (2014), "Low-Oxygen Culture Conditions Extend the Multipotent Properties of Human Retinal Progenitor Cells", Tissue Engineering, vol. 20, pp. 6362-6371.
Bjornson, C.R.R. et al. (1999) "Turning Brain into Blood: A Hematopoietic Fate Adopted by Adult Neural Stem Cells in Vivo," Science, 283:534-537.
Carter D A et al. (2009), "CD133 adult human retinal cells remain undifferentiated in Leukaemia Inhibitory Factor (LIF)", BMC Ophthalmology, 9:1.
Claes et al. (2004) IOVS, 45:2039-2048.
Coles B L K et al. (2004), "Facile isolation and the characterization of human retinal stem cells", Proceedings of the National Academy of Sciences, vol. 101, No. 44, p. 15772-15777.
Communication from European Patent Office issued in corresponding application No. 13 749 143.7 dated Apr. 25, 2016.
Coutu et al., "Roles of FGF signaling in stem cell self-renewal, senescence and aging", vol. 3, No. 10, Oct. 2011, pp. 920-933.
Diloreto et al. (1996) Experimental Neurology, 140:37-42.
Eriksson, P.S. et al. (1998) "Neurogenesis in the Adult Human Hippocampus," Nature Med., 4(11):1207, 1313-1317.
Extended European Search Report dated Mar. 19, 2019, from application No. 18207320.5.
Extended European Search Report dated Jul. 10, 2015 for European Application No. 13749143.7.
Extended European Search Report dated Jul. 7, 2015 for EP Application No. 13741481.9.
Final Office Action dated Jun. 25, 2018, from U.S. Appl. No. 14/379,239.
Final Office Action for U.S. Appl. No. 12/266,116 dated Jun. 23, 2016, 12 pages.
Flax et al., "Engraftable Human Neural Stem Cells Respond to Developmental Cues, Replace Neurons, and Express Foreign Genes," Nature Biotech, vol. 16 pp. 1033-1039.
Gage et al., "Survival and Differentiation of Adult Neuronal Progenitor Cells Transplanted to the Adult Brain," Proc. Natl. Acad. Sci. USA, 92:11879-11883.
Haurta, et al., (IVOS, Mar. 15, 1999, vol. 40, No. 4. pp. S728).
Herrera, M.B. et al. (2006) "Isolation and Characterization of a Stem Cell Population from Adult Human Liver," Stem Cells 24:2840-2850.
Ikawa et al. (1995) "Green Fluorescent Protein as a Marker in Transgenic Mice," Development Growth and Differentiation, Japanese Society of Developmental Biologists, 37(1):455-459.
International Preliminary Report on Patentability for International Application No. PCT/US2016/026286, dated Feb. 21, 2014, 19 pages.
International Preliminary Report on Patentability issued in corresponding application No. PCT/US2013/022494 dated Aug. 7, 2014.
International Search Report (ISA/US) for International Application No. PCT/US2013/022494, dated Apr. 1, 2013, 2 pages.
International Search Report (ISA/US) for International Application No. PCT/US2013/026286, dated Apr. 25, 2013, 2 pages.
Jensen, A.M. et al. (1997) "Continuous Observation of Multipotential Retinal Progenitor Cells in Clonal Density Culture," Devel. Biology, 188:267-279.
Kelley, Matthew W., et al., "Regulation of Proliferation and Photoreceptor Differentiation in Fetal Human Retinal Cell Cultures", Investigative Ophthalmology and Visual Science, 1995, vol. 36, pp. 12-80-1289.
Klassen et al. (2004) IOVS, 45:4167-4173.
Klassen H et al. (2007), "Progenitor Cells from the Porcine Neural Retina Express Photoreceptor Markers after Transplantation to the Subretinal Space of Allorecipients", Stem Cells, 25(5); pp. 1222-1230.
Klassen H J et al. (2004), "Multipotent Retinal Progenitors Express Developmental Markers, Differentiate into Retinal Neurons, and Preserve Light-Mediated Behavior", Invest. Opthalmol. Vis. Sci., 45(11), pp. 4167-4173.
Klassen, H. et al. (2004) "Isolation of Retinal Progenitor Cells From Post-Mortem Human Tissue and Comparison With Autologous Brain Progenitors", Journal of Neuroscience Research 77:334-343.
Koholodenko et al., "Anti-apoptotic effect of retinoic acid on retinal progenitor cells mediated by a protein kinase A-dependent mechanism" Cell Research, vol. 17, 2007, pp. 151-162.
Koso, H., et al. "SSEA-1 marks regionally restricted immature subpopulations of embryonic retinal progenitor cells that are regulated by the Wnt signaling pathway", Developmental Biology 292 (2006) 265-276.
Lu et al. (2002) Brain Research, 943:292-300.
Luo, et al., "Human Retinal Progenitor Cell Transplantation Preserves Vision," The Journal of Biological Chemistry, vol. 289, No. 10, pp. 6362-6371, Mar. 7, 2014.
McFarlane et al. (1998) Development, 125:3967-3975.
Minanov et a. (1997) Transplantation, 64:182-186.
Nagashima et al. (1981) Acta Neuropathol., 53:333-336.
Nishikawa, A. et al. (1998) "Clonal Adult Hippocampus-Derived Stem Cells Can Migrate Into Injured Adult Rat Retina," Retinal Transplantation II, 39(4):519 (Abstract 77).
Non-Final Office Action dated Sep. 4, 2019, from U.S. Appl. No. 14/379,239.
Non-Final Office Action for U.S. Appl. No. 14/379,239 dated Jan. 4, 2016. 19 pages.
Non-Final Office Action dated Mar. 24, 2016 for U.S. Appl. No. 14/373,881.
Okabe et al., 1997, FEBS Letters, 407: 313-319.
Osborne et al. (1999) Survey of Ophthalmology, 43:S102-S128.
Ostenfeld et al. (2002) Developmental Brain Research, 134:43-55.
Palmer, T.D. et al. (1997) "The Adult Rat Hippocampus Contains Primordial Neural Stems Cells," Molecular and Cellular Neurosci., 8:389-404.
Pera et al. (2000) Journal of Cell Science, 113:5-10.
Perron, M. et al. (2000) "Retinal Stem Cells in Vertebrates," Bioessays, 22(8):685-688.
Pruszak, Jan et al. "Markers and Methods for Cell Sorting of Human Embryonic Stem Cell-Derived Neural Cell Populations", Sep. 2007, NIH Public Access.
Redenti et al (2008), "Retinal tissue engineering using mouse retinal progenitor cells and a novel biodegradable, thin-film poly(e-

(56) References Cited

OTHER PUBLICATIONS caprolactone) nanowire scaffold", Journal of Ocular Biology, Diseases, and Informatics, vol. 1, No. 1, p. 19-29.
Redenti, S. et al. (2009) "Engineering retinal progenitor cell and scrollable poly(glycerol-sebacate) composites for expansion and subretinal transplantation," Biomaterials 30(20):3405-3414.
Reh et al., 1998, J. Neurobiol., 36: 206-220.
Ross et al. (1995) Histology, A Text and Atlas, 3rd edition, Williams and Wilkins: Baltimore:749-756.
Sanghera, et al., "The PI3K/Akt/mTOR pathway mediates retinal progenitor cell survival under hypoxic and superoxide stress", Molecular and Cellular Neuroscience, 2011, 47, pp. 145-153.
Shihabuddin, L.S. et al. (1995) "The Adult CNS Retains the Potential to Direct Region-Specific Differentiation of a Transplanted Neuronal Precursor Cell Line," J. of Neursic., 15(10):6666-6678.
Shihabuddin, L.S. et al. (1997) "FGF-2 is Sufficient to Isolate Progenitors Found in the Adult Mammalian Spinal Cord," Experimental Neurology, 148:557-586.
Sodha S et al (2011), "Microfabrication of a three-dimensional polycaprolactone thin-film scaffold for retinal progenitor cell encapsulation", Journal of Biomaterials Science, Polymer Edition VSP BV Netherlands, vol. 22, No. 4-6, p. 443-456.
Stern et al. (2006) Retinal Repair by Stem Cell Transplantation, Springer: London:259-280.
Suhonen, J.O. et al. (1996) "Differentiation of Adult Hippocampus-Derived Progenitors into Olfactory Neurons in Vivo," Nature, 383:624-627.
Takahashi et al., "Transplantation of Neural Stem Cells into Injured Adult Rat Retina," Journal of Japanese Ophthalmological Society, vol. 102, 1998, p. 174 (Abstract III-2-19).
Takashi, M. (1998) "Widespread Integration and Survival of Adult-Derived Neural Progenitor Cells in the Developing Optic Retina," Molecular and Cellular Neurosci., 12:340-348.
Tao, S. et al. (2007) "Survival, migration and differentiation of retinal progenitor cells transplanted on micro-machined poly(methyl methacrylate) scaffolds to the subretinal space," Lab Chip 7(6):695-701.
Tropepe, V. et al. (2000) "Retinal Stem Cells in the Adult Mammalian Eye," Science, 287:2032-2036.
U.S. Advisory Action dated Jun. 15, 2006 for U.S. Appl. No. 10/203,105.
U.S. Advisory Action dated Oct. 17, 2007 for U.S. Appl. No. 10/203,105.
U.S. Final Office Action dated Dec. 2, 2005 for U.S. Appl. No. 10/203,105.
U.S. Final Office Action dated Jul. 10, 2013 for U.S. Appl. No. 13/356,073.
U.S. Final Office Action dated Jul. 8, 2008 for U.S. Appl. No. 10/203,105.
U.S. Final Office Action dated Mar. 27, 2007 for U.S. Appl. No. 10/203,105.
U.S. Final Office Action dated Nov. 7, 2014 in U.S. Appl. No. 12/266,116.
U.S. Final Office Action dated Apr. 12, 2010 for U.S. Appl. No. 12/266,116.
U.S. Non-Final Office Action dated Dec. 28, 2009 for U.S. Appl. No. 12/266,116.
U.S. Non-Final Office Action dated Jan. 28, 2008 for U.S. Appl. No. 10/203,105.
U.S. Non-Final Office Action dated Mar. 1, 2005 for U.S. Appl. No. 10/203,105.
U.S. Non-Final Office Action dated Mar. 1, 2013 for U.S. Appl. No. 13/356,073.
U.S. Non-Final Office Action dated Mar. 20, 2014 for U.S. Appl. No. 12/266,116.
U.S. Non-Final Office Action dated Nov. 25, 2015 for U.S. Appl. No. 12/266,116.
U.S. Non-Final Office Action dated Jul. 3, 2013 for U.S. Appl. No. 12/666,166.
U.S. Non-Final Office Action dated Sep. 19, 2006 for U.S. Appl. No. 10/203,105.
U.S. Notice of Allowance dated Aug. 25, 2008 for U.S. Appl. No. 10/203,105.
U.S. Office Action dated Oct. 31, 2017, from U.S. Appl. No. 14/379,239.
U.S. Restriction Requirement dated Dec. 8, 2004 for U.S. Appl. No. 10/203,105.
U.S. Restriction Requirement dated Jan. 18, 2013 for U.S. Appl. No. 13/356,073.
U.S. Restriction Requirement dated Sep. 18, 2015 for U.S. Appl. No. 14/379,239.
Van Hoof et al. (2006) Molecular and Cellular Proteomics, 5:1261-1273.
Whiteley et al. (1996) Experimental Neurology, 140:100-104.
Yang et al., "In Vitro Isolation and Expansion of Human Retinal Progenitor Cells", Experimental Neurology, vol. 177, No. 1, 2002, pp. 326-331.
Yuan et al., "Cell-Surface Marker Signatures for the Isolation of Neural Stem Cells, Glia and Neurons Derived from Human Pluripotent Stem Cells," PLo5 ONE, vol. 6, issue 3, Mar. 2011, 16 pages.
Zahir et al., 2005, Stem Cells, 23: 424-432.
Zhang et al. (1998) Investigative Ophthalmology and Visual Science, 39:1021-1027.

\* cited by examiner

PHENOTYPE PROFILE OF HUMAN RETINAL PROGENITOR CELLS

CROSS-REFERENCE TO RELATED APPLICATIONS

This application is a Continuation Application of U.S. application Ser. No. 14/379,239, filed on Feb. 15, 2013, which is a national stage application under 35 U.S.C. § 371 International Application No. PCT/US2013/026286, filed Feb. 15, 2013, which in turn claims the benefit under 35 U.S.C. § 119(e) of U.S. Provisional Application Ser. No. 61/600,288, filed Feb. 17, 2012, the content of each of which are hereby incorporated by reference into this application in their entireties.

BACKGROUND OF THE INVENTION

The degeneration of the human retina, either as a result of trauma, age or disease, can result in permanent visual loss and affect millions of people worldwide. Degenerative conditions include, for instance, retinitis pigmentosa, age-related macular degeneration and diabetic retinopathy. These conditions are characterized by the progressive death of light sensing photoreceptor cells of the retina, and are the leading causes of incurable blindness in the western world. As the intrinsic regenerative capacity of the human retina is extremely limited, the only viable treatment option for people suffering from photoreceptor cell loss is cellular replacement.

Several cell types have been suggested as cell therapy tools for retinal degenerative disorders. Such cell types include human retinal progenitor cells (hRPC), retinal pigment epithelial cells, glial progenitors, neural stem cells, bone marrow and cord blood derived cells. Multipotent stem cells (also variously referred to as progenitor cells, immature cells, precursor cells, undifferentiated cells or proliferative cells) are an active focus for transplantation and differentiation.

Human retinal progenitor cells have great potential for use in clinical applications, such as for transplantation into degenerative or diseased retinal hosts. Such cells are typically isolated from fetal retina in pre- and post-natal tissue by removing the ciliary marginal zone and the optic nerve to eliminate contamination. See, for instance, U.S. Pat. No. 7,514,259, the disclosure of which is incorporated by reference herein. These cells can be expanded in vitro, and are capable of migrating into and repopulating the retina, forming new functioning photoreceptors.

The use of live cells as a drug product in clinical applications such as for transplantation requires the comprehensive characterization of the cell population during the expansion of the host population and prior to injection of the cells in a human recipient. Such characterization is typically achieved by identification of specific markers expressed on the surface of the cell. The identification of specific markers, i.e. markers unique to the particular cell line, is also useful for the enrichment or depletion of the host population.

Various attempts have been made in the past to identify specific markers unique to different cell types. Cell populations which have been successfully characterized and identified in this way include hematopoietic stem cells, embryonic stem cells, neural stem cells and glial progenitor cells.

Carter et al., BMC Ophthalmology, 9:1, 2009, describes the use of the marker CD133 to purify adult human retinal cells. Retinal cell suspensions were derived from adult human postmortem tissue, and were enriched with magnetic automated cell sorting. Cell purification of about 95% was demonstrated.

U.S. Pat. No. 6,468,794 describes the enrichment of neural stem cell and progenitor cell populations using monoclonal antibodies that bind to cell surface markers. U.S. Pat. No. 7,015,037 describes isolated multipotent stem cells that are surface negative for the markers CD44, CD45, HLA Class I and HLA Class II. See, also, U.S. Pat. Nos. 6,908,763, 7,749,754 and 7,781,179, all of the respective disclosures of which are incorporated by reference herein.

Yuan et al., Plos One, 6(3), el 7540, March 2011, describes improved differentiation and enrichment procedures that generate highly pure populations of neural stem cells, glia and neurons derived from pluripotent stem cells. Cell surface signatures or markers are identified on the cells to enable the isolation of the cells from heterogeneous differentiating cell populations by fluorescent activated cell sorting. In particular, the reference states that a population of neural stem cells has been successfully isolated by using fluorescence activated cell sorting (FACS) and the following markers: CD184+, CD271−, CD44− and CD24+. The disclosure of this publication is hereby incorporated by reference herein in its entirety.

In spite of various attempts to characterize different types of stem cells using cell-specific markers, surface markers specific for human retinal progenitor cells have not been identified. The successful identification of such markers would advance the technology by permitting the enrichment of cell populations, the elimination of less desirable cells from the culture, such as glial cells, neural cells and retinal pigment epithelial cells, and the ultimate selection of retinal progenitor cells highly expressing the markers of interest. The highly purified cell populations can then be cultured using techniques such as those described in U.S. patent application Ser. No. 13/160,002, filed Jun. 14, 2011, and manufactured into cell banks for the purposes of deriving cells that could be used in human transplantation for the treatment of degenerative diseases of the retina. The cell surface markers can represent markers that allow characterization of the cell product to be delivered to the patient, in partial fulfillment of the requirements by government regulatory agencies for defining cell product quality.

In view of the aforementioned, as well as the importance of human retinal progenitor cells for clinical evaluation and use, it will readily be appreciated that a need exists to improve the characterization, identification and purification of human retinal progenitor cells for transplantation and disease treatment. These and other objectives of the invention will be clear from the following description.

SUMMARY OF THE INVENTION

The invention is directed to a purified human retinal progenitor cell and/or substantially homogenous populations of human retinal progenitor cells and methods for obtaining said cell and/or substantially homogeneous cell populations. The human retinal progenitor cells of the invention are uniquely characterized by the presence of each of the following cell surface markers: SSEA4, CD73, PTK7 and PSA-NCAM. In a further aspect, the cells are characterized by the expression of recoverin, Sox2 and Pax 6. Compositions containing the cells and/or populations are further disclosed herein.

In one aspect, the human retinal progenitor cells of the invention are further characterized as lacking the following surface markers: CD15, CD133, A2B5 and CD38 (also identified in the art as CD15−, CD133−, A2B5− and CD38−.) CD15 and CD133 are neural stem cell surface markers. A2B5 and CD38 are glial progenitor cell surface markers. In a further aspect, the purified cell populations of the invention comprise at least about 50%, preferably at least about 60%, and most preferably at least about 80%, of the human retinal progenitor cells specifically identified with the indicated cell surface markers. Compositions containing the cells and/or populations are further disclosed herein.

The method of the invention includes the steps of obtaining an isolated cell sample from human tissue and identifying and then isolating or purifying the progenitor cell by use of the markers identified above, using methods known to the skilled artisan. In one aspect, the method comprises, or alternatively consists essentially of, or yet further consists of, removing the various impurities and contaminants normally present in the cell sample, sorting the cells to separate and purify the human progenitor cells having the above-identified surface markers, and collecting the purified cells for clinical or experimental use. The cells can subsequently be placed into tissue culture and grown to permit substantial cell numbers to be generated for therapy, as described in U.S. patent application Ser. No. 13/160,002, filed Jun. 14, 2011, the disclosure of which is incorporated by reference herein. Cell sorting techniques which can be used in the practice of the invention are generally known and include, for instance, flow cytometry, and specifically fluorescence activated cell sorting using antibodies and fragments thereof that recognize and bind to the cell surface markers.

The method of the invention permits the selection of retinal progenitor cells from a variety of human tissue sources, such as bone marrow, cord blood, human embryonic stem cells or their differentiated progeny, human induced pluripotent stem cells or their differentiated progeny, although the preferred tissue sources are human adult or fetal retina tissue.

The human retinal progenitor cells of the invention have various therapeutic uses, such as for the treatment of retinal diseases upon transplantation into a diseased eye, and the cells can be autologous or allogeneic to the host patient or recipient. The cells of the invention can also be used for in vitro drug discovery and toxicity testing, by contacting the cells with pharmaceutical agents in an appropriate assay format. Because the retinal progenitor cells are capable of differentiating into photoreceptor cells, they are useful for replacing or repairing photoreceptor tissue in a patient and, e.g., for the treatment of degenerative diseases of the eye such as retinitis pigmentosa, age-related macular degeneration and diabetic retinopathy. Thus, the present disclosure also provides methods for preparing a purified culture of photoreceptor cells by culturing a cell or population of cells identified above under appropriate conditions to induce or support differentiation of the cells to photoreceptor cells. Various agents can then by contacted with the cells (at one or more times during the differentiation of the cell or population) to determine the effect, if any on the cell's viability, characteristics or differentiation.

The foregoing embodiments and aspects of the invention are illustrative only, and are not meant to restrict the spirit and scope of the claimed invention.

BRIEF DESCRIPTION OF THE DRAWINGS

The foregoing and other advantages and features of the invention will become apparent upon reading the following detailed description with reference to the accompanying figures and drawings.

DETAILED DESCRIPTION OF THE EMBODIMENTS

Figure 1:
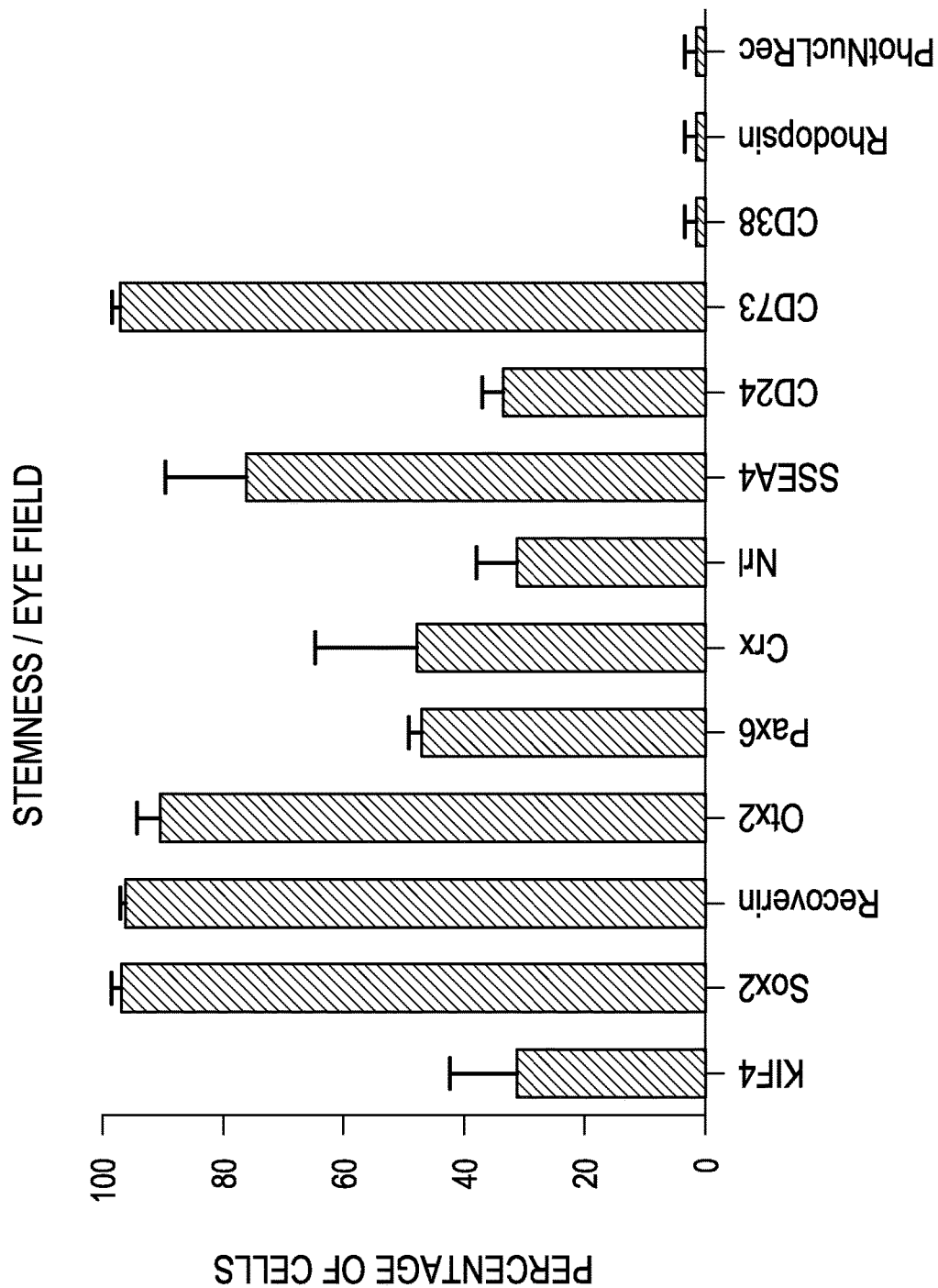
FIG. 1 is a bar graph showing the expression of the indicated stemness/eye field markers based on a flow cytometry analysis of human retinal progenitor cells.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, flow cytometry and cell sorting which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gaited. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology. See, also, Yuan et al., Plos One, 6(3), el 7540, March 2011.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated, that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transitional terms are within the scope of this invention.

A "host" or "patient" of this invention is an animal such as a mammal, or a human. Non-human animals subject to diagnosis or treatment are those in need of treatment such as for example, simians, murines, such as, rats, mice, canines, such as dogs, leporids, such as rabbits, livestock, sport animals, and pets.

The terms "purified" or "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. A purified or isolated cell is separated from tissue in which it is normally associated with in nature. An isolated or purified cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types (pluripotent). Recently, somatic cells, including fully differentiated adult cells such as fibroblasts, can become pluripotent like embryonic stem cells, by means of the introduction of some or all of the following factors: Oct-3/4, SOX2, c-Myc, Nanog and Klf4. These cells are referred to as induced pluripotent stem cells (IPSCs). An embryonic or induced pluripotent stem cell is one that has been cultured under in vitro conditions that allow proliferation without differentiation for months to years. Pluripotent stem cells can be distinguished from other types of cells by the use of appropriate markers including, but not limited to, Oct-4, alkaline phosphatase, CD30, TDGF-1, GCTM-2, Genesis, Germ cell nuclear factor, SSEA1, SSEA3, and SSEA4.

The term "stem cell" also includes "dedifferentiated" stem cells, an example of which is a somatic cell which is directly converted to a stem cell, i.e. reprogrammed. A clone is a line of cells that is genetically identical to the originating cell; in this case, a stem cell.

The term "propagate" or "proliferate" means to grow or alter the phenotype of a cell or population of cells. The term "growing" or "expanding" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue. In yet another embodiment, the tissue is comprised of cardiomyocytes.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

"Clonal proliferation" or "clonal expansion" refers to the growth of a population of cells by the continuous division of single cells into two identical daughter cells and/or population of identical cells.

As used herein, the "lineage" of a cell defines the heredity of the cell, i.e. its predecessors and progeny. The lineage of a cell places the cell within a hereditary scheme of development and differentiation.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type or phenotype. "Dedifferentiated" defines a cell that reverts to a less committed position within the lineage of a cell. As used herein, the term "differentiates or differentiated" defines a cell that takes on a more committed ("differentiated") position within the lineage of a cell.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention.

The antibodies can be polyclonal or monoclonal and can be isolated from any suitable biological source, e.g., murine, rat, sheep and canine.

The term "antibody" is further intended to encompass monoclonal antibodies, digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')2 fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The terms "monoclonal antibody" or "monoclonal antibody composition" as used herein refer to a preparation of antibody molecules of single molecular composition. A monoclonal antibody composition displays a single binding specificity and affinity for a particular epitope.

"Retinal progenitor cells", or "neuroretina-derived retinal stem cells", or "retinal stem cells", as those terms are used herein, are synonymous and mean isolated viable stem cells which can be derived from neuroretinal tissue. The point of origin of these cells is one factor that can distinguish them from non-neural retinal cells, such as pigmented cells of the retinal pigment epithelium, the ciliary body or the iris. The cells of the invention are further distinguished by an inability to proliferate in the absence of growth factors. The cells do not express significant amounts of photoreceptor markers in normal growth culture, but in the absence of growth factors and particularly when plated on certain matrix material (PCL patent appl), the cells rapidly differentiate into cells positive for photoreceptor markers.

The cells of the invention are still further characterized by the unique set of cell surface markers as further described herein. The cells of the invention can derived from either pre-natal or post-natal sources, and are multipotent, meaning they are capable of self-renewal and retina-specific differentiation into photoreceptors. Such cells are more also described in U.S. Pat. No. 7,514,259, the disclosure of which is incorporated by reference herein in its entirety.

As used herein in connection with the retinal progenitor cells of the invention, the term "multipotency", means the ability of the retinal progenitor cells to proliferate and form mature retinal cell types, particularly photoreceptor cells.

"Substantially homogeneous" cell population describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype is determined by the cell surf ace markers described in more detail herein.

As used herein, the terms "treating," "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., macular degeneration. As is understood by those skilled in the art, "treatment" can include systemic amelioration of the symptoms associated with the pathology and/or a delay in onset of symptoms such as chest pain. Clinical and subclinical evidence of "treatment" will vary with the pathology, the individual and the treatment.

A "composition" is intended to mean a combination of active agent, cell or population of cells and another compound or composition, inert (for example, a detectable agent or label) or active.

A "pharmaceutical composition" is intended to include the combination of an active agent with a carrier, inert or active such as a biocompatible scaffold or matrix, making the composition suitable for diagnostic or therapeutic use in vitro, in vivo or ex vivo.

The term "pharmaceutically acceptable carrier" (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

An "effective amount" is an amount sufficient to effect beneficial or desired results. An effective amount can be administered in one or more administrations, applications or dosages.

As used herein, the term "administering" for in vivo and ex vivo purposes means providing the subject with an effective amount of the composition, cells or populations effective to achieve the desired object of the method. Methods of administering composition such as those described herein are well known to those of skill in the art and include, but are not limited to parenteral, topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the cell used for therapy, composition used for therapy, the purpose of the therapy, and the subject being treated. Single or multiple administrations can be carried out with the dose level and pattern being selected by the treating physician. For example, the compositions can be administered prior to or alternatively to a subject already suffering from a disease or condition for which the treatment is intended.

Retinal Progenitor Cell Surface Markers

The invention relates to a purified or isolated cell and/or substantially homogeneous populations of retinal progenitor cells characterized by the presence of each of the following cell surface markers: SSEA4+, CD73+, PTK7+ and PSA-NCAM+.

These are positive surface markers, meaning that each marker is present on the surface of the cell and its presence can be detected by an antibody or other relevant ligand that binds to the surface marker. The retinal cells of the invention are also characterized by negative cell markers, meaning that the presence of the markers cannot be detected (or the absence of the markers are observed) by an antibody to the marker. The following are the negative cell markers for the retinal progenitor cells of the invention: CD15− (neural stem cell), CD 133− (neural stem cell), A2B5− (glial progenitor cell), and CD38− (glial progenitor cell).

The cell populations of the invention typically have at least about 50%, preferably at least about 60%, and most preferably at least about 80%, of human retinal progenitor cells. Human sources for the retinal progenitor cells include tissue from various organs or tissue, such as pre-natal retinal tissue, fetal tissue, adult organs and bone marrow, and the retinal neurosphere. Human retinal tissue is the preferred source of these cells. The cells can be from living viable hosts or cadavers.

Briefly, human retinal progenitor cells are isolated from different donations of human neural retina at 16 weeks gestational age, obtained from ethically and GTP compliant tissue banks, for example ABR Inc of Alameda, California. The isolated and dissociated cells are expanded on a fibronectin-coated surface in ULTRACULTURE™ medium with supplements (20 ng/ml rhEGF, 10 ng/ml bFGF) up to different passages for example PS and Pl3, then frozen to provide stocks of Drug Substance (DS) lots. These Drug Substance lots can be manufacture to GMT) for clinical application. For cell preparation, DS lots were thawed and plated at a density of 20,000 cells/sq·cm. Two days later, cells were harvested and prepared according to standard procedures to generate the Drug Product (DP). The cell concentration (actual number of cells per mL) and cell viability (stability) for each prepared batch of human retinal progenitor cells is recorded.

For characterization, the human retinal progenitor cells are prepared as a fresh suspension of retinal cells in a non-toxic excipient, such as HBSS-NAC, at a concentration of 50 million cells per mL. The cells are expanded and prepared according to standard procedures for transplantation. See, in general, the method described in U.S. application Ser. No. 13/160,002, filed Jun. 14, 2011, the full disclosure of which is incorporated by reference herein.

The cells can be characterized using flow cytometry analysis and immunocytochemical analysis as described below in the examples.

Therapeutic Uses

This invention also provides methods for replacing or protecting photoreceptor cells in a patient in need of this treatment comprising implanting the human retinal progenitor cells described above in a sub-retinal space of a diseased or degenerated human retina. In one aspect, the cells can treat or alleviate the symptoms of retinitis pigmentosa in a patient in need of the treatment. In another aspect, the cells can be seeded onto appropriate biocompatible scaffolds, such as described in U.S. patent application Ser. No. 13/356,073, filed Jan. 23, 2012, the disclosure of which is incorporated by reference herein, and the cell-scaffold combination product can be implanted in order to treat or alleviate the symptoms of age related macular degeneration in a patient in need of this treatment. For all of these treatments, the retinal progenitor cells are allogeneic to the patient. In a further aspect, the cells of the invention can be administered in combination with other treatments.

Screening Assays

The present invention provides methods for screening various agents that modulate the differentiation of a retinal progenitor cell. It could also be used to discover therapeutic agents that support and/or rescue mature photoreceptors that are generated in culture from retinal progenitor cells. For the purposes of this invention, an "agent" is intended to include, but not be limited to, a biological or chemical compound such as a simple or complex organic or inorganic molecule, a peptide, a protein (e.g. antibody), a polynucleotide (e.g. anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated, that the agent is used alone or in combination with another agent, having the same or different biological activity as the agents identified by the inventive screen.

To practice the screening method in vitro, an isolated population of cells can be obtained as described above. When the agent is a composition other than a DNA or RNA, such as a small molecule as described above, the agent can be directly added to the cells or added to culture medium for addition. As is apparent to those skilled in the art, an "effective" a mount must be added which can be empirically determined. When the agent is a polynucleotide, it can be directly added by use of a gene gun or electroporation.

Alternatively, it can be inserted into the cell using a gene delivery vehicle or other method as described above. Positive and negative controls can be assayed to confirm the purported activity of the drug or other agent.

Kits

This disclosure also provides a kit for use in the methods described herein containing one or more of the population, cell or composition of the invention and instructions for use. Optionally, the kit can include reagents for use in the methods.

In an alternative aspect, the disclosure provides for kits for use in the methods described herein comprising instructions for isolation or purified of the cells or populations and instructions for use and optionally reagents to isolate or purified a cell or population of cells from a suitable tissue source as described herein.

The invention may be further described and illustrated in the following examples which are not intended to limit the scope of the invention thereby.

EXAMPLES

Retina Morphology

The morphology of the neural retina which is the subject of this invention is further described in commonly assigned co-pending U.S. application Ser. No. 13/160,002, filed Jun. 14, 2011, the full disclosure of which is incorporated by reference herein.

Cell Isolation hRPCs (human retinal progenitor cells) were isolated from fetal retinas as described, with small modifications, in the following references: Klassen, H. J. et al., Multipotent Retinal Progenitors Express Developmental Markers, Differentiate into Retinal Neurons, and Preserve Light-Mediated Behavior, Invest. Opthalmol. Vis. Sci., 2004, 45(11), pages 4167-4173; Klassen, H. et al., Isolation of Retinal Progenitor Cells from Post-Mortem Human Tissue and Comparison with Autologous Brain Progenitors, J. Neuroscience Research, 2004, 77(3), pages 334-343; Klassen, H. et al., Progenitor Cells from the Porcine Neural Retina Express Photoreceptor Markers after Transplantation to the Subretinal Space of Allorecipients; Stem Cells, 2007, 25(5); pages 1222-1230.

Briefly, whole neuroretinas from human fetal eyes (14-18 weeks gestational age) were dissected, dissociated in 0.1% collagenase I (Sigma) during 4 cycles (1.5 hour of fermentation in total), and plated in modified ULTRACULTURE™ media (10 ng/ml rhEGF, 20 ng/ml rhbFGF, Pen/strep, Nystatin and L-glutamine) or frozen. The amount and viability of single cells and clumps were estimated using Trypan blue and a haemocytometer.

Flow Cytometry Analysis

Human retinal progenitor cells are processed according to the following general protocol:
1. Fixation: Use cold fresh buffered 4% paraformaldehyde pH 7.4 for all antigens (except cell cycle analysis and PCNA) for 30 minutes at 4° C. Use 100% ethanol for cell cycle analysis and PCNA for 30 minutes at 4° C.
2. Wash: Add PBS and spin at 1500 rpm for 5 minutes.
3. Permeabilization and Block: Resuspend pellet in blocking buffer (0.1% Triton-X, 10% goat serum solution, prepared in 5% BSA in PBS), incubate for 30 minutes at room temperature.
4. Wash
5. Resuspend pellet in X (number of antibodies to be added) 100 fll of staining buffer (10% goat serum solution, prepared in 5% BSA in PBS). Aliquot by 100111 in 5 ml tubes.
6. Add primary antibodies according to Table 1 below. All antibody solutions were prepared in staining buffer. Incubate for 45 minutes at room temperature.
7. Wash
8. Add100 fll of secondary antibody (in staining buffer) according to Table 1. Incubate for 30 minutes at room temperature.
9. Wash
10. Resuspend in 500 fll of PBS.
11. Analyze within 4 hours (using, for instance, BD LSR II) at least 10,000 events within the gate.

Propidium Iodide Staining (for Cell Cycle Analysis)
1. Suspend the cell pellet in 1 mL PBS containing 20 flg/mL of PI and 100 flg/mL of DNase-free RNase A
2. Wash
3. Resuspend in 500 f..tl of PBS and analyze.

DAPI Staining (for Viability Analysis)
1. Before fixation, resuspend cells in 200 ng/ml DAPI in PBS.
2. Incubate for 5 minutes at room temperature.
3. Wash
4. Fix in 4% cold PFA for 30 minutes.
5. Wash
6. Resuspend in 500f..ll of PBS and analyze.

TABLE 1

| | Antigen | Host | Company | Reference | Dilution, 1: |
|---|---|---|---|---|---|
| Eye field | Nrl | ms | Santa Cruz | sc-166087 | 50 |
| | SSEA4 | ms | Chemicon | MAB4304 | 100 |
| | Klf4 | rbt | SantaCruz | sc-20691 | 50 |
| | Sox2 | rbt | Santa Cruz | sc-20088 | 50 |
| | Nestin | ms | BD Bio. | 611658 | 100 |
| | Pax6 | ms | hybridoma bk | | 100 |
| | Otx2 | rbt | Chemicon | AB9566 | 100 |
| Proliferation | CyclinD1 | rbt | Neomarkers | RB010P1abx | 100 |
| | PCNA | ms | Dako | M0879 | 100 |
| | Ki67 | rbt | Chemicon | AB9260 | 100 |
| Photoreceptors | Nr2e3(PNR) | rbt | Chemicon | AB9469 | 200 |
| | Recoverin | rbt | Chemicon | AB5585 | 200 |
| | Rhodopsin | ms | Chemicon | MABN15 | 100 |
| | Opsin Blue | rbt | Chemicon | AB5407 | 100 |
| | Opsin Red/Gr | rbt | Chemicon | AB5405 | 100 |
| | S-opsin | rbt | Abcam | ab81017 | 100 |
| Neurons/Glia | NF200 | rbt | Chemicon | AB1982 | 100 |
| | GFAP | ms | Chemicon | MAB360 | 100 |
| | B3tubulin | ms | Sigma | T8669 | 100 |
| Surface Markers | CD15/SSEA1 | ms | BD Bio. | 5590945 | 100 |
| | CD24 | PE | MACS | | 100 |
| | CD73 | PE | MACS | | 50 |
| | CD133 | PE | MACS | | 50 |
| | PSA-NCAM | PE | MACS | | 50 |
| | CD38 | PE | MACS | | 50 |
| | SSEA4 | ms | Chemicon | MAB4304 | 100 |
| Isotype Controls | Iso IgG | rbt | Invitrogen | | |
| | Iso IgG1 | ms | Invitrogen | | |
| | Iso IgG2 | ms | Invitrogen | | |

Statistical Methods

The ratio of positive cells is determined based on isotype control for antibodies. The experiment is repeated three times and an average percentage of positive cells with standard deviation is calculated for each marker. Also, the ratio of high expression/low expression cells is calculated where applicable.

Results

Flow Cytometry

Results of flow cytometry analysis (3 runs, 10,000 events each) are presented in the following Table 2. The numbers in the table show the ratio of positive (expressing) cells within the drug product, based on a comparison with the appropriate isotype control. A 98% level of expression of the isotype was chosen as the threshold level.

TABLE 2

| Klf4 | Sox2 | Recoverin | Otx2 | Pax6 | Crx | Nrl | SSEA4 | CD24 | CD73 |
|---|---|---|---|---|---|---|---|---|---|
| 51.4 | 97.7 | 97.1 | 94.3 | 50.1 | 48.0 | 31.0 | 91.2 | 38.8 | 98.1 |
| 12.7 | 99.2 | 97.2 | 94.9 | 46.7 | 77.9 | 43.6 | 89.4 | 35.0 | 98.7 |
| 27.6 | 97.3 | 97.0 | 82.3 | 44.5 | 19.1 | 18.2 | 49.3 | 27.1 | 97.1 |

| CD38 | Rhodopsin | PhotNucLRec | Ki67 | PCNA | CyclinD1 | Cycle: | Cycle: | Cycle: | Beta3tubulin |
|---|---|---|---|---|---|---|---|---|---|
| 2.3 | 1.30 | 0.8 | 82.8 | 96.7 | 34.4 | 70.6 | 3.2 | 25.1 | 92.9 |
| 5.2 | 4.10 | 3.4 | 80.3 | 86.9 | 28.1 | 70.7 | 17.0 | 12.3 | 99.4 |
| 0.9 | 2.00 | 1.6 | 75.2 | 91.8 | 22.5 | 70.1 | 5.6 | 23.9 | 99.3 |

| NF200 | Nestin | GFAP | PSA- | PTK7 | SSEA1/CD | CD133 | A2B5 |
|---|---|---|---|---|---|---|---|
| 97.7 | 95.1 | 14.8 | 62.1 | 97.8 | 0.7 | 5.8 | 2.15 |
| 97.9 | 98.9 | 40.9 | 49.4 | 98.6 | 0.8 | 2.8 | 4.20 |
| 90.1 | 99.4 | 11.6 | 97.8 | 99.7 | 2.3 | 1.4 | 3.30 |

Figure 2:
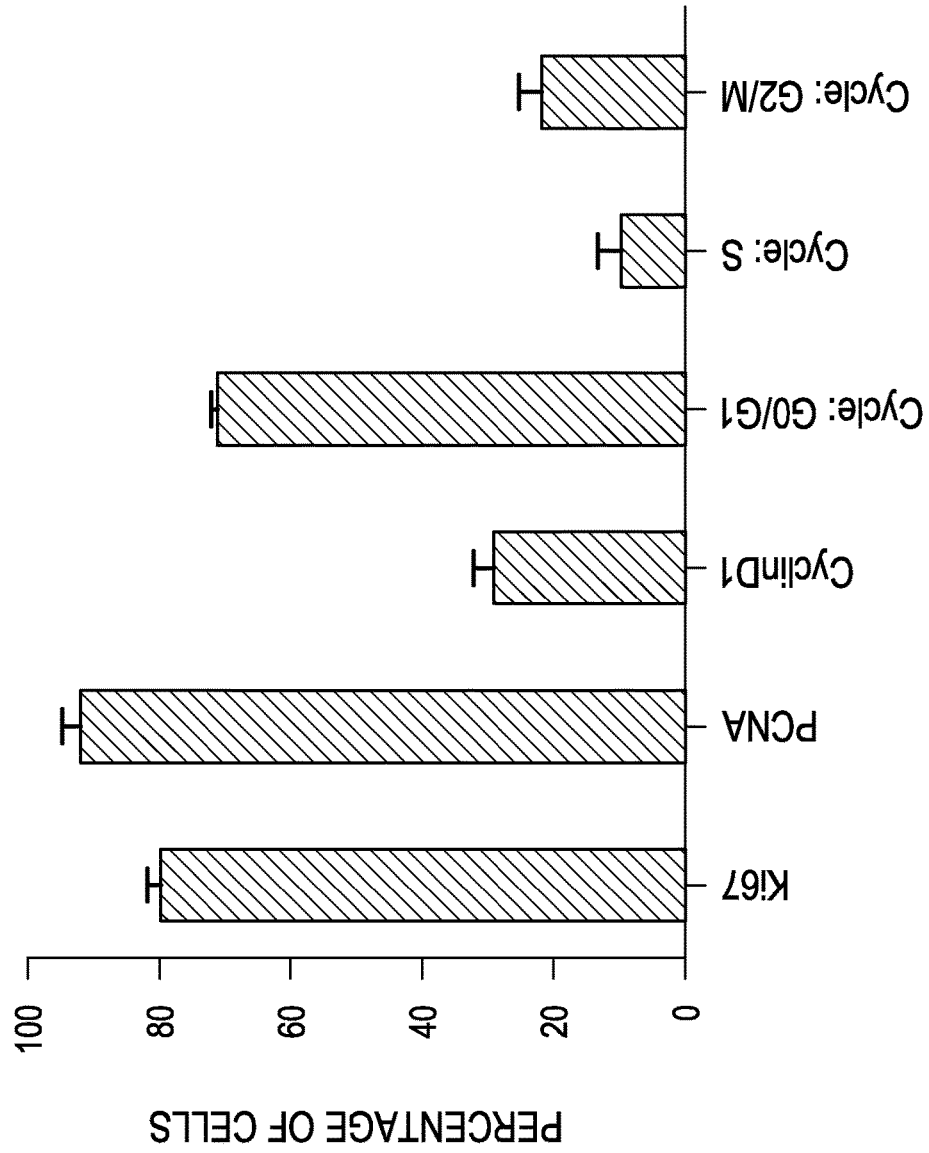
FIG. 2 is a bar graph showing the expression of the indicated proliferative/cell cycle markers based on a flow cytometry analysis of human retinal progenitor cells.
Figure 3:
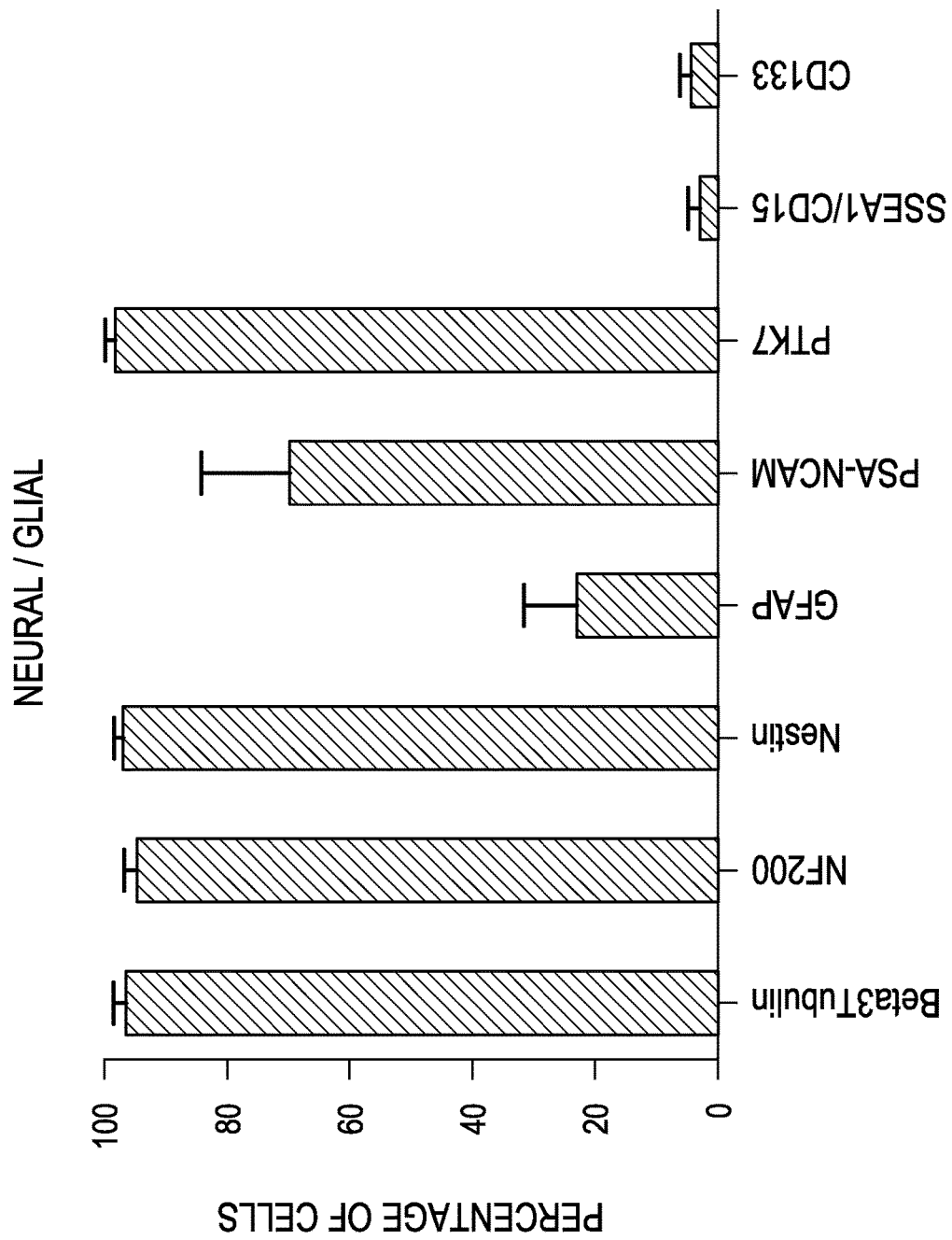
FIG. 3 is a bar graph showing the expression of the indicated neural/glial markers based on a flow cytometry analysis of human retinal progenitor cells.

FIGS. 1, 2 and 3 are bar graphs illustrating the mean and standard deviation (M+/−SEM) of the above results. The cells in a drug product have been found to express most of the sternness markers investigated. However, only half of the parent population is positive for Pax6, Crx and Nrl, suggesting that this population actually consists of several subpopulations. The markers are stable across increase passages from 9 to 14, and across two separate fetal donations.

Immunocytochemical Analysis

Human retinal progenitor cells are processed according to the following general protocol:
1. Plating: Cells are plated onto freshly fibronectin-coated 16-well Nunc slides at a density of 4 k cells/sq. cm. in human retinal progenitor cell media (200 fll/well).
2. Incubation: 6 hours at 37° C., 5% CO2, 3% O2, 100% humidity.
3. Wash: Aspirate media and add PBS.
4. Fixation: Cold, buffered 4% PFA for 10 minutes at room temperature.
5. Wash
6. Permeabilization and Block: Incubate in blocking buffer (0.1% Triton-X, 10% goat serum solution, prepared in 5% BSA in PBS) for 1 hour at room temperature.
7. Wash
8. Add primary antibodies according to Table 3 (50 fll/well). All antibody solutions are prepared in staining buffer (10% goat serum solution, prepared in 5% BSA in PBS). Incubate overnight at 4° C. in humidified chamber.
9. Wash 2 times, 5 minutes each.
10. Add 50 fll of secondary antibody (in staining buffer) according to Table 3. Incubate for 1 hour at room temperature.
11. Wash 3 times, 5 minutes each.
12. Mount in mounting media w/DAPI.
13. Dry overnight.
14. Image and analyze.

TABLE 3

|  | Antigen | Host | Company | Reference | Dilution, 1: |
|---|---|---|---|---|---|
| Eye field | Nrl | ms | Santa Cruz | sc-166087 | 50 |
|  | SSEA4 | ms | Chemicon | MAB4304 | 200 |
|  | Klf4 | rbt | Santa Cruz | sc-20691 | 50 |
|  | Sox2 | rbt | Santa Cruz | sc-20088 | 50 |
|  | Nestin | ms | BD Bio. | 611658 | 200 |
|  | Pax6 | ms | hybridoma |  | 200 |
|  | Otx2 | rbt | Chemicon | AB9566 | 200 |
|  | Chx10 | Gt | Santa Cruz | sc-21692 | 200 |
|  | CD15/SSEA | ms | BD Bio. | 559045 | 200 |
| Proliferation | CyclinD1 | rbt | Neomarkers | RB010P1ab | 200 |
|  | PCNA | ms | Dako | M0879 | 200 |
|  | Ki67 | rbt | Chemicon | AB9260 | 200 |
| Photoreceptors | Nr2e3(PNR) | rbt | Chemicon | AB9469 | 200 |
|  | Recoverin | rbt | Chemicon | AB5585 | 200 |
|  | Rhodopsin | ms | Chemicon | MABN15 | 100 |
|  | Opsin Blue | rbt | Chemicon | AB5407 | 200 |
|  | Opsin | rbt | Chemicon | AB5405 | 200 |
|  | S-opsin | rbt | Abcam | ab81017 | 200 |
| Neurons/Glia | NF200 | rbt | Chemicon | AB1982 | 200 |
|  | GFAP | ms | Chemicon | MAB360 | 200 |
|  | Vimentin | ms | Sigma | T8660 | 200 |
|  | B3tubulin | ms | Sigma | V22558 | 200 |
| Isotope Controls | Iso IgG | rbt | Invitrogen |  |  |
|  | Iso IgG1 | ms | Invitrogen |  |  |
|  | Iso IgG2 | ms | Invitrogen |  |  |

Results

Immunocytochemistry

Figure 4:
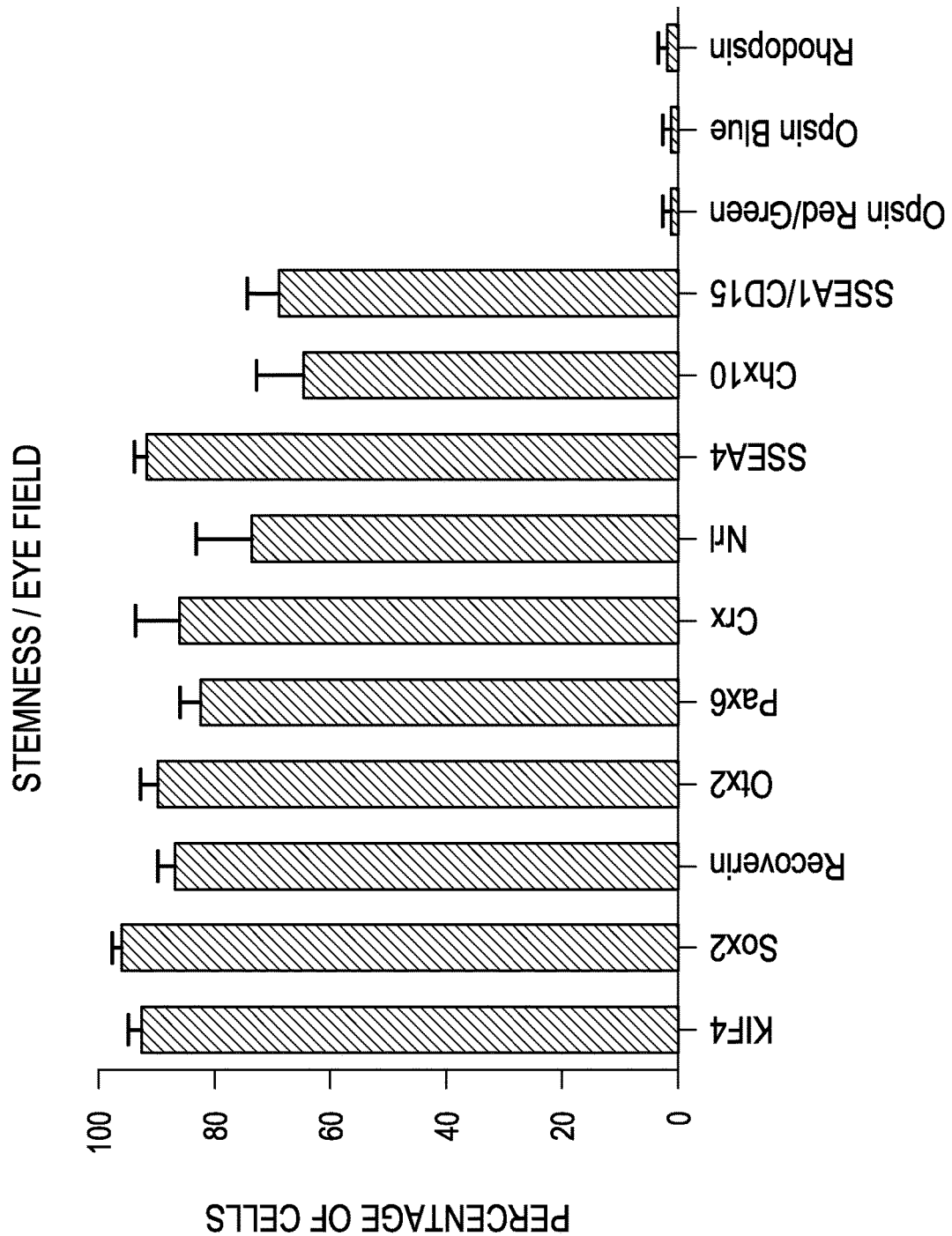
FIG. 4 is a bar graph showing the expression of the indicated stemness/eye field markers based on an immunocytochemical analysis of human retinal progenitor cells.
Figure 5:
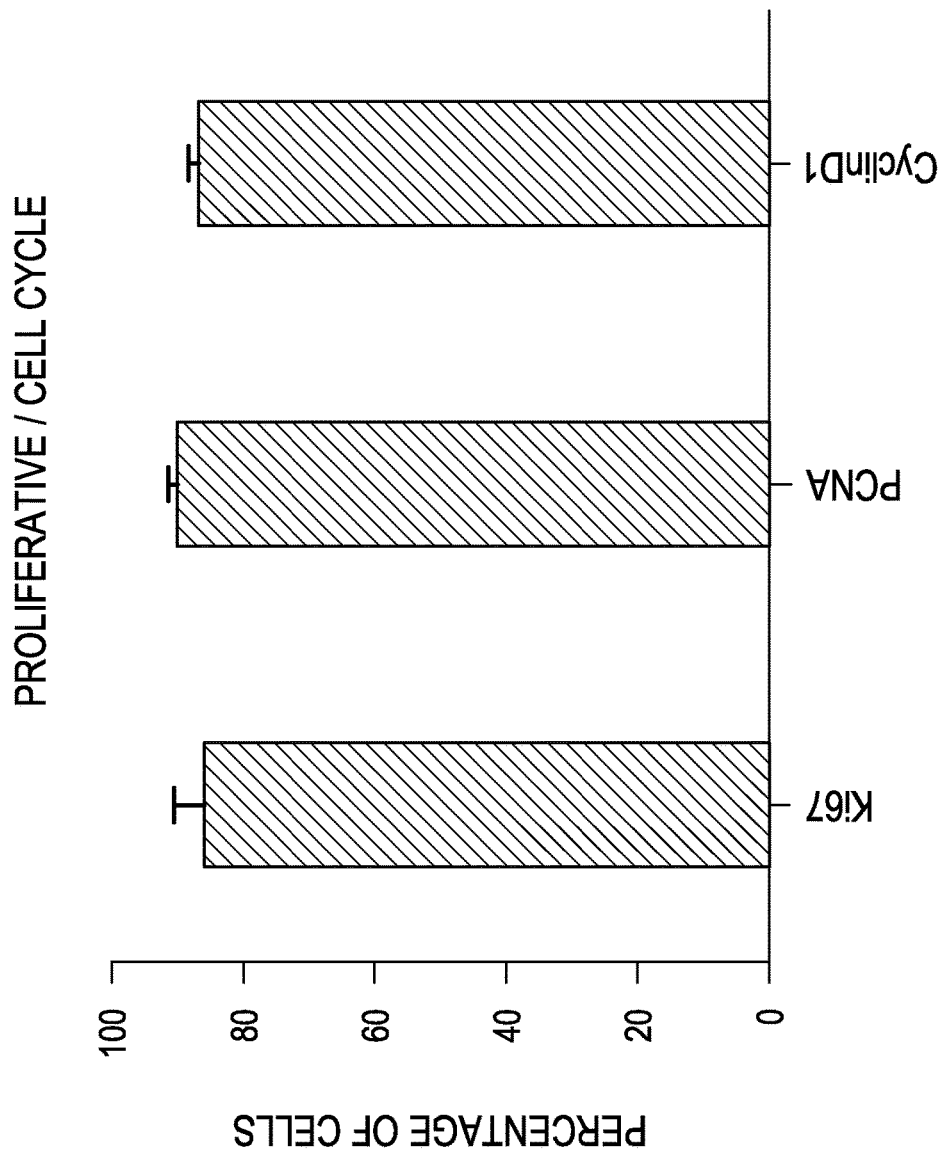
FIG. 5 is a bar graph showing the expression of the indicated proliferative/cell cycle markers based on an immunocytochemical analysis of human retinal progenitor cells.
Figure 6:
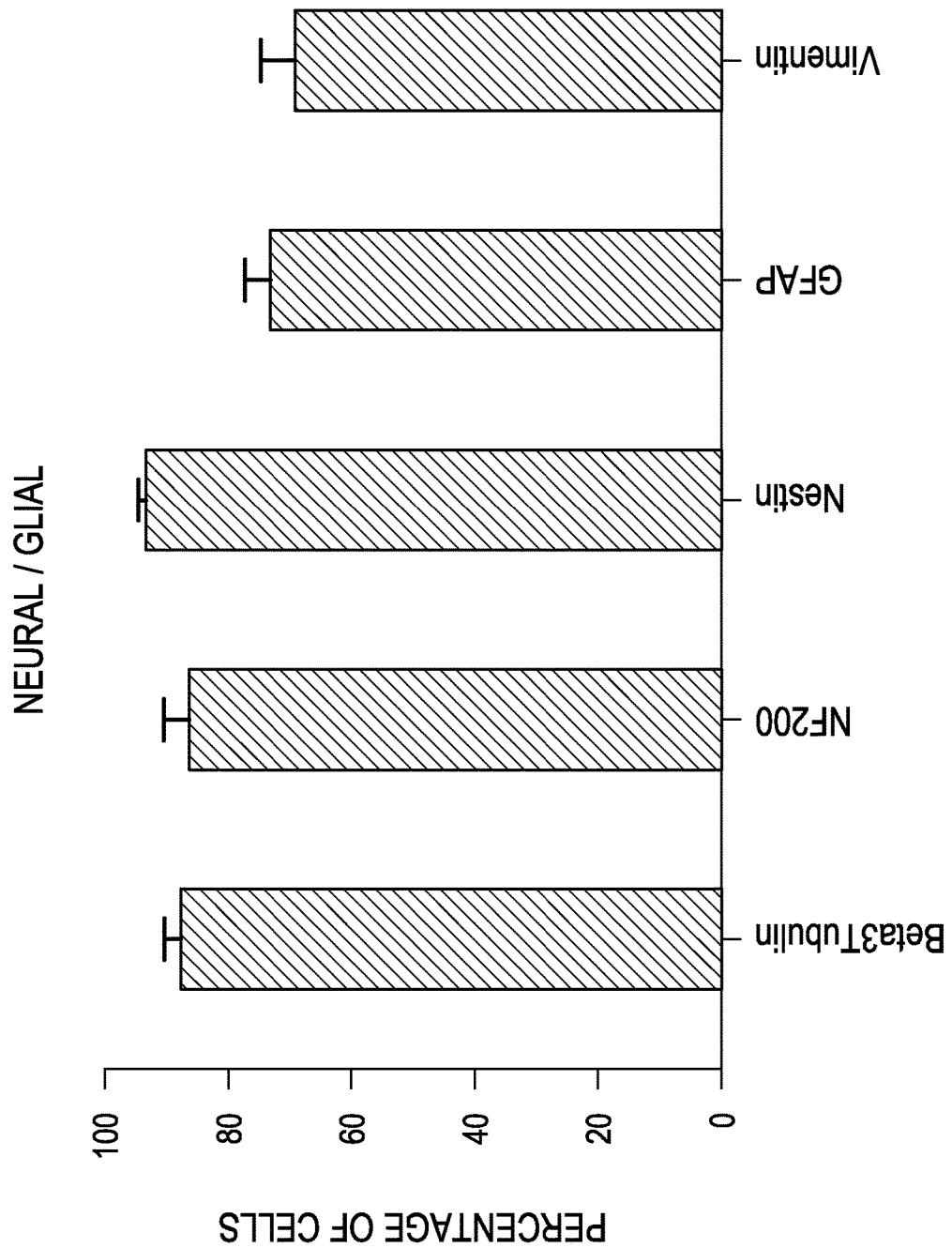
FIG. 6 is a bar graph showing the expression of the indicated neural/glial markers based on an immunocytochemical analysis of human retinal progenitor cells.

Results of immunocytochemical analysis (5 runs, >100 events each) are presented in FIGS. 4, 5 and 6. Fluorescence and exposure settings on the microscope/camera were adjusted using appropriate isotype control. FIGS. 4, 5 and 6 are bar graphs illustrating the mean and standard deviation (M+/−SEM) of the above results. The results from the immunocytochemistry analysis supports and adds to the profile established using flow cytometry.

The human retinal progenitor cells of this invention may be used for studying the development of the retina and eye, as well as factors affecting such development, whether beneficially or adversely. These hRPCs can also be used for clinical trials by transplantation into a suffering retina from dysfunctions of the eye. They may be used advantageously to repopulate or to rescue a dystrophic and degenerated ocular tissue, particularly a dysfunctional retina. Retinal dysfunction encompasses any lack or loss of normal retinal function, whether due to disease, mechanical or chemical injury, or a degenerative or pathological process involving the recipient's retina. The hRPCs may be injected or otherwise placed in a retinal site, the subretinal space, vitreal cavity, or the optic nerve, according to techniques known in the art.

Advantageously, the hRPCs of the invention may be used to compensate for a lack or diminution of photoreceptor cell function. Examples of retinal dysfunction that can be treated by the retinal stem cell populations and methods of the invention include but are not limited to: photoreceptor degeneration (as occurs in, e.g., retinitis pigmentosa, cone dystrophies, cone-rod and/or rod-cone dystrophies, and macular degeneration); retina detachment and retinal trauma; photic lesions caused by laser or sunlight; a macular hole; a macular edema; night blindness and color blindness; ischemic retinopathy as caused by diabetes or vascular occlusion; retinopathy due to prematurity/premature birth; infectious conditions, such as, e.g., CMV retinitis and toxoplasmosis; inflammatory conditions, such as the uveitis; tumors, such as retinoblastoma and ocular melanoma; and for the replacement of inner retinal neurons, which are affected in ocular neuropathies including glaucoma, traumatic optic neuropathy, detachment, and radiation optic neuropathy and retinopathy.

The treatments described herein can be used as stand alone therapies, or in conjunction with other therapeutic treatments. Such treatments can include the administration of a substance that stimulates differentiation of the neuroretina-derived stem cells into photoreceptors cells or other retinal cell types (e.g., bipolar cells, ganglion cells, horizontal cells, amacrine cells, Mueller cells).

From the foregoing, it will be appreciated that, although specific embodiments of the invention have been described herein for purposes of illustration, various modifications may be made without deviating from the spirit and scope of the invention as set forth in the appended claims. All publications, patents, and patent applications referenced herein are incorporated by reference in their entirety.

What is claimed is:

1. An expanded population of human retinal progenitor cells having been expanded in from about 10 ng/ml to about 20 ng/ml epidermal growth factor and from about 10 ng/ml to about 20 ng/ml basic fibroblast growth factor in low oxygen conditions consisting of about 3% oxygen for at least 6 hours and wherein at least 80% of the population of the cells express the following identifiable markers SOX2, Recoverin, Otx2, CD73, PCNA, Beta3tubulin, NF200, Nestin, and PTK7 but not expressing CD15 and CD133, and wherein the population is expanded for at least 8 passages.

2. A composition comprising the expanded population of claim 1 and a carrier.

3. The composition of claim 2, wherein the carrier is a pharmaceutically acceptable carrier.

4. An expanded population of human retinal progenitor cells having been expanded in from about 10 ng/ml to about 20 ng/ml epidermal growth factor and from about 10 ng/ml to about 20 ng/ml basic fibroblast growth factor in low oxygen conditions consisting of about 3% oxygen for at least 6 hours and wherein at least 90% of the population of the cells express the following identifiable markers SOX2, Recoverin, CD73, Beta3tubulin, NF200, Nestin, and PTK7 but not expressing CD15 and CD133, and wherein the population is expanded for at least 8 passages.

5. A composition comprising the expanded population of claim 4 and a carrier.

6. The composition of claim 5, wherein the carrier is a pharmaceutically acceptable carrier.

7. A method for treating or alleviating the symptoms of retinitis pigmentosa in a patient in need of said treatment, comprising administering to said patient an effective amount of one or more of the population of claim 1, thereby treating or alleviating the symptoms of retinitis pigmentosa in said patient.

8. A method for replacing or repairing or protecting photoreceptor cells in a patient in need of such treatment comprising administering to said patient an effective amount of one or more of the population of claim 1, thereby replacing or repairing or protecting photoreceptor cells in said patient.

9. A method of treating or alleviating the symptoms of age related macular degeneration in a patient in need of said treatment, comprising administering to said patient an effective amount of the cell population of one or more of the population of claim 1, thereby treating or alleviating the symptoms of age related macular degeneration in said patient.

10. A method for treating or alleviating the symptoms of retinitis pigmentosa in a patient in need of said treatment, comprising administering to said patient an effective amount of one or more of the population of claim 4, thereby treating or alleviating the symptoms of retinitis pigmentosa in said patient.

11. A method for replacing or repairing or protecting photoreceptor cells in a patient in need of such treatment comprising administering to said patient an effective amount of one or more of the population of claim 4, thereby replacing or repairing or protecting photoreceptor cells in said patient.

12. A method of treating or alleviating the symptoms of age related macular degeneration in a patient in need of said treatment, comprising administering to said patient an effective amount of the expanded cell population of claim 4, thereby treating or alleviating the symptoms of age related macular degeneration in said patient.

* * * * *